US008323196B2

(12) United States Patent
Piletskiy et al.

(10) Patent No.: US 8,323,196 B2
(45) Date of Patent: Dec. 4, 2012

(54) DEVICE FOR MEASURING INTRAOCULAR PRESSURE THROUGH AN EYELID

(76) Inventors: Gennadiy Konstantinovich Piletskiy, Ryazan (RU); Konstantin Vasilyevich Ivanischev, Ryazan (RU); Nikolai Gennadyevich Piletskiy, Ryazan (RU); Alexandr Nikolaevich Chervyakov, Ryazan (RU)

(*) Notice: Subject to any disclaimer, the term of this patent is extended or adjusted under 35 U.S.C. 154(b) by 937 days.

(21) Appl. No.: 12/227,255

(22) PCT Filed: Apr. 19, 2007

(86) PCT No.: PCT/RU2007/000195
§ 371 (c)(1),
(2), (4) Date: Nov. 12, 2008

(87) PCT Pub. No.: WO2007/133113
PCT Pub. Date: Nov. 22, 2007

(65) Prior Publication Data
US 2009/0234215 A1     Sep. 17, 2009

(30) Foreign Application Priority Data

May 12, 2006 (RU) ................................ 2006116313

(51) Int. Cl.
*A61B 3/16* (2006.01)
(52) U.S. Cl. .................... 600/405; 600/398; 600/399
(58) Field of Classification Search .............. 600/405, 600/398, 399
See application file for complete search history.

(56) References Cited

U.S. PATENT DOCUMENTS
3,934,462 A * 1/1976 Rende ........................... 600/405
(Continued)

FOREIGN PATENT DOCUMENTS
| RU | 2007951 | 2/1994 |
| RU | 2123798 | 12/1998 |
| WO | WO 03/105680 | 12/2003 |

OTHER PUBLICATIONS

Nesterov, A. P. et al. Transpalpebralny tonomer dlya izmereniya vnutriglaznogo davleniya, zh. Vestnik oftalmologii, No. 1, 2003, pp. 1-5. (ISR) (With English Translation of relevant parts).
International Search Report.

*Primary Examiner* — Brian Szmal
*Assistant Examiner* — Mehari Kidanemariam
(74) *Attorney, Agent, or Firm* — Collard & Roe, P.C.

(57) ABSTRACT

The invention relates to medicine. The inventive device for measuring intraocular tension through an eyelid comprises a body, a movable sleeve provided with a support and placed in the body in such a way that it is reciprocally displaceable for producing a static load applicable to the eyebulb through the eyelid, a rod which is provided with a flat base and is arranged in the sleeve cavity in such a way that it is displaceable with respect to the support and produces an impact action for deforming the eyebulb through the eyelid and at least one measuring coil placed in the movable sleeve. A permanent magnet is mounted on the rod and the measuring coil is disposed with respect to the magnet in such a way that it is enabled to control the direction and speed of the rod displacement and is connected to a control, processing and display unit, which is embodied in such a way that it produces opposite polarity voltage in the coil for returning the rod to the initial position thereof and for consequently creating the rod motion pulse in a direction of the support in such a way that the signal received from the measuring coil is converted and the obtained results are displayed.

8 Claims, 2 Drawing Sheets

U.S. PATENT DOCUMENTS 4,621,644 A * 11/1986 Eilers ........................... 600/405
5,176,139 A * 1/1993 Fedorov et al. ............... 600/398
6,394,954 B1 * 5/2002 Piletsky et al. ............... 600/398
6,447,449 B1 * 9/2002 Fleischman et al. .......... 600/405

* cited by examiner

DEVICE FOR MEASURING INTRAOCULAR PRESSURE THROUGH AN EYELID

CROSS REFERENCE TO RELATED APPLICATIONS

This application is the National Stage of PCT/RU2007/000195 filed on Apr. 19, 2007, which claims priority under 35 U.S.C. §119 of Russian Application No. 2006116313 filed on May 12, 2006. The international application under PCT article 21(2) was not published in English.

FIELD OF THE INVENTION

The invention relates to portable medical devices for ophthalmology designed for measuring intraocular pressure (IOP) and simultaneously applying a static load and impact force to deform the eyeball through the eyelid, and may be used during mass-scale examination of the population for glaucoma, for checking the correctness of its treatment, and for monitoring intraocular pressure individually without anesthesia and risk of infection.

BACKGROUND OF THE INVENTION

A device that is known in the art to be used for measuring intraocular pressure on an open eye comprises a probe, one part of which is made of a magnetic material and the other part, of nonmagnetic material having a rounded (hemispherical) base for deforming the eye, the probe being placed within an electromagnetic winding to impart a desired speed to it, the electromagnetic winding being built into the wall of the housing held in the operator's hand during measurement (see: Patent WO 03/105680 [PCT/F103/00489], A61B3/16, published on Dec. 24, 2003).

The prior art device for measuring IOP uses the force of impact to deform an open eye, but no static load is applied. IOP measurement through the eyelid does not give the desired accuracy because IOP measurement through the eyelid requires significantly larger energy than is used on an open eye to compensate for the shock-absorbing properties of the eyelids that have a different anatomical structure. Increasing the impact force, however, leads to instability of the spatial position of the eye because of the stretching of the muscles to which the eye is attached. Instability does not allows IOP to be measured with desired accuracy. Moreover, the rounding at the probe base is objectionable when IOP is measured through the eyelid with a large impact load as it causes excessive pain during measurement.

Also known in the art are devices for measuring IOP through the eyelid while the eye position is stabilized, for example, by applying further static load to the eye.

For example, a prior art device for measuring intraocular pressure comprises an annular support through which a static load is applied to the eye during measurement and a ball weighing 0.3 to 0.7 gram to deform the cornea of the eye through the eyelid by impact force, the ball being dropped in a free fall from a height of 120 to 150 mm, followed by measuring the pressure according to the height of the first rebound of the ball (see: Russian Patent 2,007,951, class A61B3/16, published in 1994).

The use of an annular support prevents the IOP measuring device from being attached firmly to the eye, so its accuracy is reduced significantly. Besides, a further measurement error increases sharply with the device deflected even insignificantly from the vertical during measurement.

The closest prior art of this invention is a device comprising a housing containing a bushing capable of moving therein within a limited range and provided with guides and a supporting part to apply a constant desired load; an eyeball deforming element in the form of a free-falling body provided within the interior of the bushing and capable of dropping in a free fall under the effect of its own weight to apply an impact load; a deformation element holder in the initial top position thereof in the top part of the movable bushing; a measuring winding built into the wall of the movable bushing and connected to the generator circuit to measure the movement function of the deformation element over time; a sensor to indicate the position of the movable bushing relative to the housing in the form of a mechanical catch registering the initial bottommost position of said bushing within the housing, including a spring-biased button, the clamping part of which is placed in an aperture of the housing wall for engaging the outer surface of the movable bushing, the supporting part of the movable bushing being provided with two projections having round support ends equally spaced at a distance of 7 to 10 mm from the movement axis of the free-falling body; the elastic deformation element being shaped as a rod having a flat base 1 to 7 mm$^2$ in area; and the bottom guide serving to limit the lower position of the deformation element within the movable bushing in an inoperative state (see: Russian Patent No. 2,123,798, class A61B3/16, published in 1998).

In the prior art device, an impact force is developed during measurement by a free-falling rod having a flat base 1 to 7 mm$^2$ in area, and a static load is applied to the eye through the eyelid by a movable bushing having a measuring winding built therein together with means to register the initial position of a rod impacting the eye through a support of an original design allowing the device to be firmly attached to the eye through the eyelid.

The prior art device, though, requires to be held in an absolutely vertical position during measurement and furthermore it requires the rod to be set in its initial position before measurement and several measurements to be taken to enhance accuracy, so that the measurement process lengthens, and the patient himself is unable to measure his IOP.

The low accuracy of IOP measurement by the prior art device is caused by the effect of the device housing being placed manually in a vertical position; the absence of means to automatically check the accuracy with which the device is positioned during measurement; and the error produced by the mechanical clamp developing the desired static load during measurement.

The invention is aimed at improving the operating characteristics of a device for IOP measurement through the eyelid.

SUMMARY OF THE INVENTION

The technical effect of the invention consists in enhanced accuracy of measurement by making measurement readings independent from the vertical position of the device housing; reduction in the time taken by the measurement process generally by a multiple factor; a simple and easy measurement process; and possibility for a patients to measure the IOP unassisted on his or her own.

The above technical effect is achieved in a device for measuring intraocular pressure through the eyelid, which comprises a housing; a movable bushing with a support arranged within the housing for limited reciprocation therein to apply a static load on the eyeball through the eyelid; a rod with a flat base arranged within the bushing for reciprocating relative to the support and applying an impact force to deform the eyeball through the eyelid; and at least one measuring winding arranged within the movable bushing, and which further has a permanent magnet provided on the rod; the measuring winding being positioned relative to the permanent magnet so as to control the direction and speed of magnet movement and being connected to a control, processing, and indication unit provided to produce voltage of opposite polarities across the measuring winding to withdraw the rod to the initial position and then to give the rod an pulse to move in the direction of the support, said unit being intended to convert the signal received from the measuring winding to measure intraocular pressure and display the measurement results.

The device may be provided with a contactless indicator of the desired static load being applied to the eyeball through the eyelid during measurement, said indicator being preferably designed as a sensor indicating the position of the bushing relative to the housing.

It is preferred to provide the sensor indicating the position of the movable bushing relative to the housing with a generator; an additional bushing with a cavity; and a coil, all arranged on the movable bushing and housing, respectively, to vary the inductance of the coil winding upon displacement of the movable bushing, the coil winding being connected to the generator circuit.

It is also preferred to connect the generator of the sensor indicating the position of the movable bushing relative to the housing to the control, processing, and measurement data display unit.

It is preferred to provide the rod with a base 0.2 to 1.5 mm$^2$ in area.

The support is preferably of the detachable type.

It is further preferred to make the support in the form of two inwardly curved wedge-shaped ends with a leveling annular projection provided between them at a height of 3 to 5 mm from their base.

Lastly, it is preferred to provide the movable bushing and support with respective cavities and apertures for air to escape therethrough during rod movement.

The idea of the invention consists in that the rod with a flat base 0.2 to 1.5 mm$^2$ in area moving controllably under the effect of electromagnetic field while the static load applied to the eyeball remains unchanged compresses reliably the eyelids of a different anatomical structure at the deformation point of the eyeball during measurement and, for this reason, enhances the accuracy of IOP measurement.

DESCRIPTION OF A PREFERRED EMBODIMENT

Figure 1:
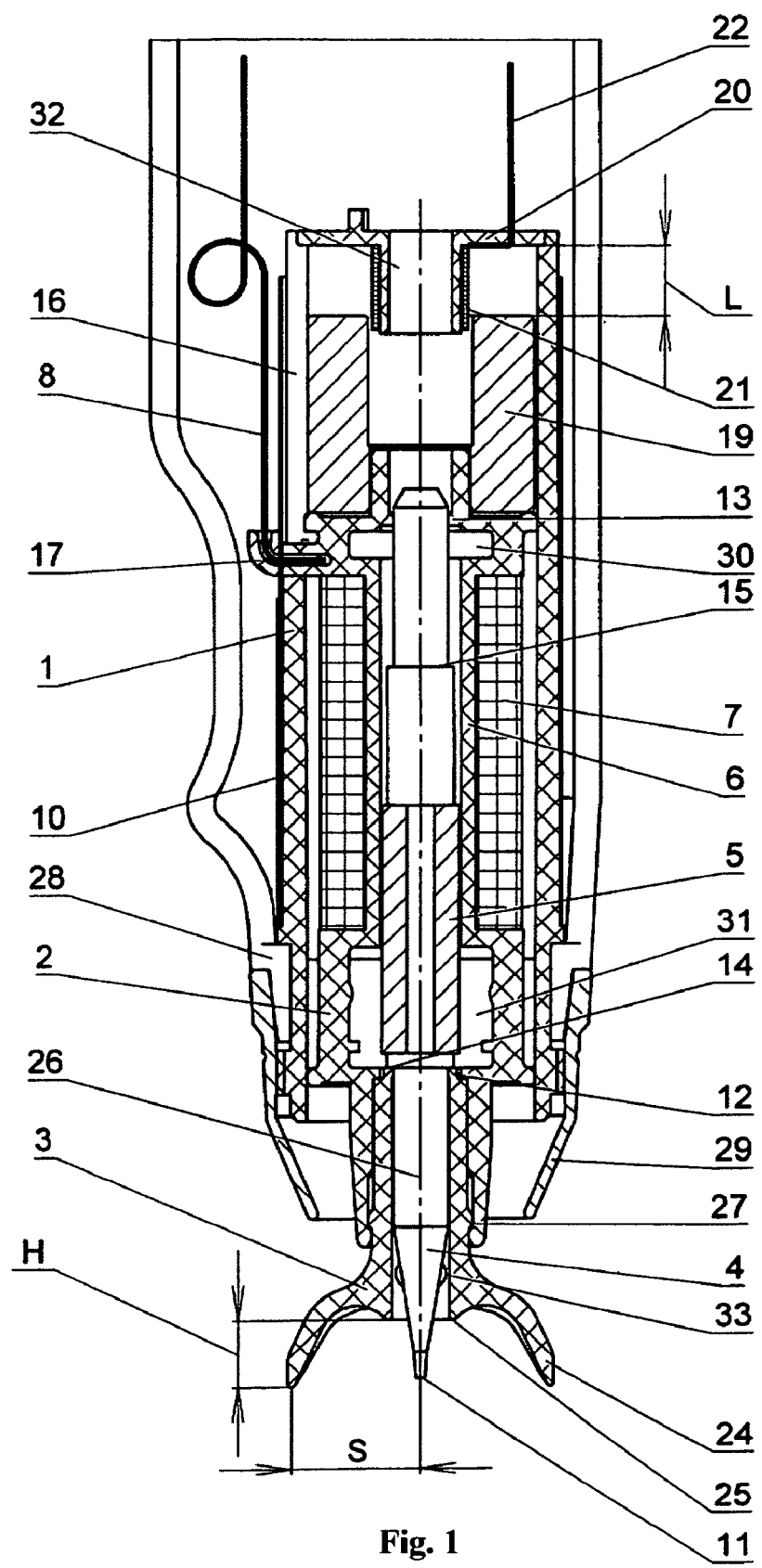
FIG. 1 is a cross-sectional view of the IOP measuring device.
Figure 2:
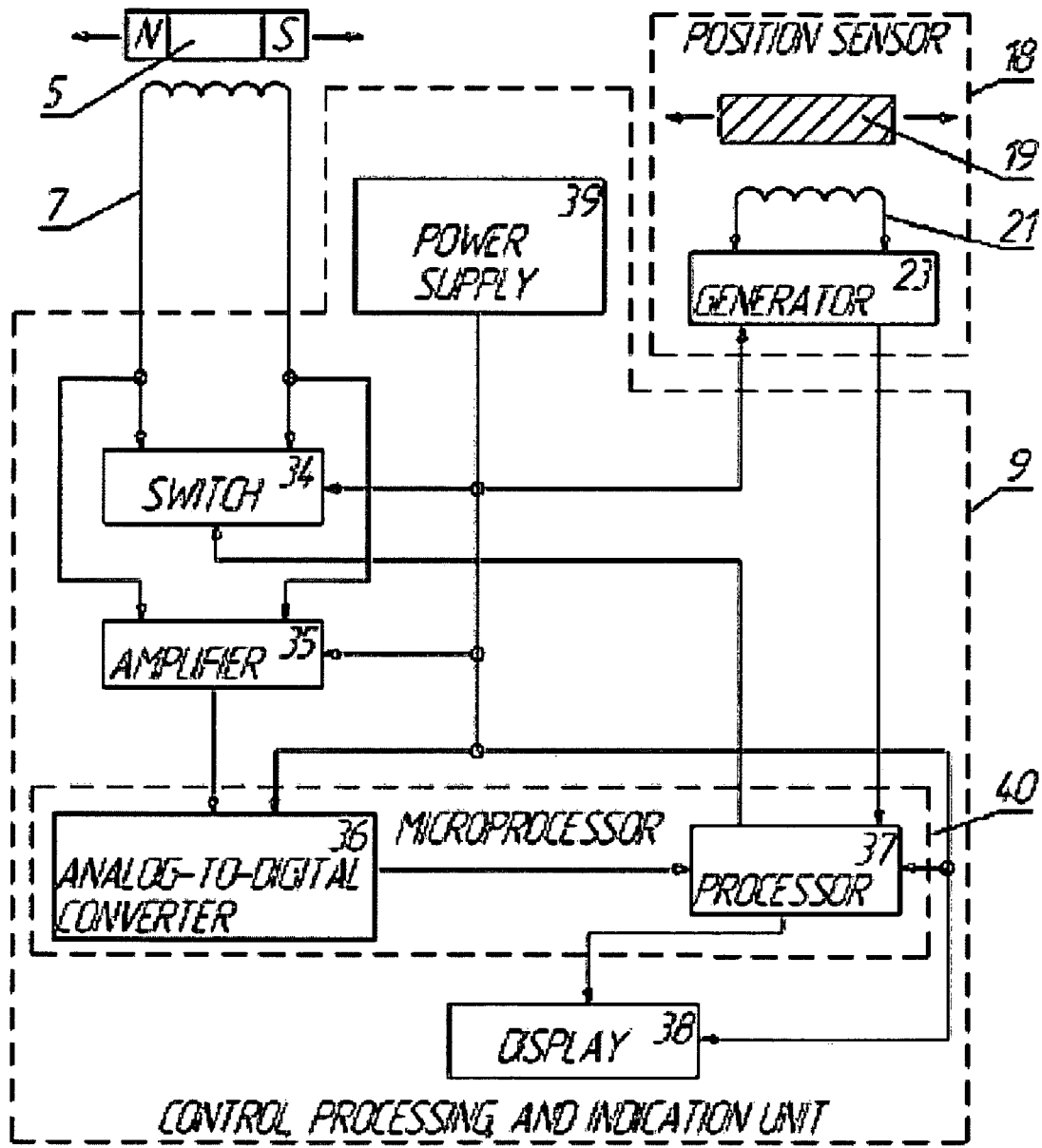
FIG. 2 is a block diagram showing the essential parts of the IOP measuring device to explain its operation.

The IOP measuring device (FIG. 1) comprises a plastics housing 1, a movable bushing 2 with a support 3 arranged within the housing 1 and adapted to reciprocate therein within a limited range to apply a static load to the eyeball through the eyelid. A rod 4 of a nonmagnetic material is provided within the movable bushing 2 to move therein relative to the support 3 and deform the eyeball through the eyelid by the force of impact. A permanent magnet 5 is provided on the rod 4. A coil 6 is arranged within the wall of the movable bushing 2 and provided with at least one measuring winding 7 arranged in relation to the permanent magnet 5 so as to control the direction and speed of movement of the rod 4. The measuring winding 7 is connected by a lead 8 to a control, processing, and indication unit 9 (FIG. 2). A protective screen 10 provided on the outside of the housing 1 is used to screen the measuring winding 7 of the coil 6.

The rod 4 is made of plastics and has a flat base 11 that is 0.2 to 1.5 mm$^2$ in area. An area smaller than 0.2 mm$^2$ is likely to cause the sensation of pain during measurement, while an area larger than 1.5 mm$^2$ does not allow the thickened eyelids to be compressed reliably. A lower and an upper sliding-friction bearings 12 and 13 are provided on the movable bushing 2 to allow the rod 4 to move freely lengthwise within the coil 6 and support 3. The downward fall of the rod 4 is limited by the surface 14 of the lower sliding-friction bearing 12. The return of the rod 4 to the initial upper position within the movable bushing 2 is limited by a surface 15 of a projection of the rod 4 and the upper sliding-friction bearing 13.

The housing 1 is provided with a longitudinal slot 16 for a stop 17 that is integrated with the movable bushing 2 to limit its vertical reciprocation and prevent its rotation relative to the housing 1. The measuring winding 7 is connected to the control, processing, and indication unit 9 by the lead 8, a part of which extends through the interior of the stop 17.

The IOP measuring device is provided with a contactless indicator of a desired static load being applied to the eye through the eyelid, for example, a sensor 18 to indicate the position of the movable bushing 2 relative to the housing 1. The sensor 18 comprises an additional bushing 19 and a stationary coil 20 fitted on the movable bushing 2 and housing 1, respectively, the winding 21 of the stationary coil 20 being connected by a lead 22 to the circuit of the generator 23 that is connected to the control, processing, and indication unit 9 (FIG. 2).

The weight of the static load (consisting of the weight of the movable bushing 2 together with its support 3, the measuring winding and additional bushing 19, and the weight of the rod 4 and the permanent magnet 5) required for measurement purposes must be varied between 20 and 30 grams. A weight under 20 grams does not allow the eyeball to be maintained in a stable and steady position, while a weight above 30 grams results in a significant increase in the tonometric pressure because of superfluous deformation of the eyeball.

The support 3 has two wedge-shaped projections 24 having rounded supporting ends, with an annular projection having a leveling area 25 at a height (H) of 3 to 5 mm from the base thereof, extending between the projections. The wedge-shaped projections 24 of the support 3 are equally spaced at a distance (S) of 7 to 10 mm from the reciprocation axis 26 of the rod 4. For easy disinfection, the support 3 is of a detachable type. The support 3 is fitted on the lower portion of the movable bushing 2 by an elastic catch 27 that allows, when necessary, the support 3 to be turned around its own axis and be removed for the rod 4 to be pulled out for maintenance and cleaning.

The housing 1 may be placed in a detachable protective plastics casing 28 secured firmly to the housing 1 by a decorative bushing 29. In this case, the protective casing 28 and the housing 1 are arranged to reciprocate together vertically relative to the movable bushing 2 and its support 3 to a distance (L) of 4 to 6 mm.

The movable bushing 2, stationary coil 20, and support 3 have cavities 30, 31, and 32, respectively, and apertures 33 to exhaust air displaced by the moving rod 4.

The control, processing, and indication unit 9 comprises a switch 34, an amplifier 35, an analog-to-digital converter 36, a processor 37, a display 38, and a power supply 39. The first and second leads of the switch 34 are connected, respectively, to the first and second inputs of the amplifier 35, which has its output connected to the first input of the analog-to-digital converter 36. The processor 37 has its first, second, and third inputs connected to the outputs of the analog-to-digital converter 36 and generator 23, and the first input of the display 38, respectively, and its first and second outputs, to the third input of the switch 34 and the second input of the display 38, respectively. The power supply 39 is connected to the input of the generator 23, the fourth input of the switch 34, the third inputs of the amplifier 35 and processor 37, respectively, and to the second input of the analog-to-digital converter 36.

The first and second inputs of the switch 34 serve as the first and second inputs of the control, processing, and indication unit 9, and are connected by the lead 8 to the measuring winding 7. The fourth input of the switch 34 is the third input of the control, processing, and indication unit 9 and is connected to the generator 23, which has its output connected to the input of the processor 37 and serves as the input of the unit 9. The analog-to-digital converter 36 and processor 37 form a microprocessor 40. The switch 34 is intended to reverse the flow of current in the measuring winding 7 in order to reverse the direction of movement of the rod 4 and apply a measured impact force to the eyeball, and is controlled by the microprocessor 40.

The present invention is based on the use of impact force to deform the eyeball through the eyelid and simultaneous application of a stable static load that keeps the eyeball in an invariable position during measurement. The operating principle of the IOP measuring device consists in imparting a measured movement pulse to the rod 4 to deform the eyeball through the eyelid and converting the reciprocation of the rod (as a result of response from the elastic surface of the eye) to electric current signals.

INDUSTRIAL APPLICABILITY

The present device for measuring intraocular pressure through the eyelid operates as follows. A patient's head is positioned face up. For the eyeball to be deformed in the sclera region, the direction of his sight is set at an angle of approximately 45° to the horizontal, using, for example, the patient's hand as a reference point. As the activated device is held by the protective casing 28 in a vertical position, the support 3 is placed on the gristle region of the upper eyelid symmetrically about the center of the eyeball, the wedge-shaped projections 24 touching the eyeball eyelid. The wedge-shaped projections 24 and the leveling area 25 of the support 3 secure the eyelid and the eyeball in a position that remains constant during all measurements. The protective casing 28 and the housing 1 are then slowly lowered to a distance of 4 to 6 mm relative to the support 3. As a result, the movable part of the device (comprising the movable bushing 2 with the measuring winding 7, the additional bushing 19, and the support 3) is moved up relative to the housing. The additional bushing 19 made of, for example, brass, moves over the stationary coil 20, changing the inductance of the winding 21 and, therefore, the frequency of the generator 23, being connected to it by the lead 22.

As the generator 23 reaches a specified frequency, the control, processing, and indication unit 9 applies automatically a direct current voltage of specified polarity through the lead 8 to the measuring winding 7, to cause the rod 4 to be moved up by the electromagnetic field to its initial position. The weight of the movable part of the device applies a desired static load to the eyeball through the eyelid. At this point, the downward movement of the housing 1 relative to the support 3 is to be discontinued, and the protective casing 28 with the housing 1 to be kept motionless in this position (for not more than 3 seconds).

At this very time, the direct-current voltage applied previously to the measuring winding 7 of the coil 6 is read off automatically and a short voltage of opposite polarity is applied. As a result, the rod 4 receives a measured pulse forcing it to move toward the eyeball and deform the eyelid and eyeball with its flat base 11 and then to rebound in the opposite direction.

As the permanent magnet 5 provided on the rod 4 moves down (toward the eyeball) and up (on rebound from the eyeball) it induces in the measuring winding 7 of the coil 6 a voltage that is then amplified in the amplifier 35 and is used to convert into digital readings, process and analyze the speed function of the rod, and is finally displayed as an IOP measurement result on the display 38.

While the device is in operation, the upper and lower sliding-friction bearings 13 and 12 allow the rod 4 to move freely lengthwise within the coil 6 and support 3. The downward free fall of the rod 4 is limited by the surface 14 of the lower sliding-friction bearing 12, and the upward movement of the rod 4 to its topmost position is limited by the surface 15 of the projection of the rod 4 and the upper sliding-friction bearing 13. An aperture 33 provided in the support 3, the cavities 30 and 31 of the movable bushing 2, and the cavity 32 of the stationary coil 20 allow air to be exhausted during the movement of the rod 4. The stop 17 placed in the longitudinal slot 16 of the housing 1 prevents rotation of the movable bushing 2 about its own axis.

The analog signal read off the measuring winding 7 is converted to digital form, and the operating mode, digital processing, and analysis of the movement function of the rod 4 are controlled according to a program by the microprocessor 40 integrated into the control, processing, and indication unit 9.

The claimed device helps to reliably compress the eyelids of varying thickness and enhances the stability of the static load applied to the eye during measurement (owing to the use of a contactless load value indicator and generation of an automatic measurement command), as a result of which the accuracy of IOP measurement is enhanced. The permanent magnet 5 fitted on the rod 4 helps replace the impact force of a free-falling rod (as in the closest related prior art) with controllable movement of the rod 4 by electromagnetic force. This reduces significantly the need for the device to be held in a vertical position during measurement and allows the rod to be reset to its initial position automatically and several IOP measurements to be taken while the device is positioned on the eye.

The IOP measuring device, in which the correctness of the static load setting is checked during measurement is convenient because it combines all necessary components in a common housing measuring not more than 175 by 26 by 20 mm and weighing up to 100 grams.

The claimed IOP measuring device is distinguished by its informative accuracy of static load setting during IOP measurement and, therefore, its measurement accuracy and speed are improved. The measurement procedure causes no pain. The device measures intraocular pressure in mm Hg with an accuracy of +/−2 mm Hg. Measurement does not take more than a second.

Taking multiple IOP measurements on a single patient during a 24 hour period at minimal costs in time is very important in verifying the correctness of a chosen treatment method and allows the efficiency of verification to be enhanced. Moreover, the risk of infection during measurement is prevented because of the absence of direct contact with the eye sclera.

The simple design of the claimed device allows it to be manufactured at an affordable price, and the ease of using it makes it possible to use the device at home as well as in clinic. The claimed invention helps enhance the accuracy of IOP measurement and monitor changes in pressure by the patient himself during treatment.

The device offers the following advantages:
- high accuracy of measurement;
- reduction in the overall IOP measurement time;
- possibility for the patient to measure IOP unassisted;
- reduction in the time needed to manipulate the device into a working position;
- application of the device in any conditions without giving specialized training to the personnel;
- improved consumer properties (such as comfort, simplicity in use, and stability of parameters); and
- easy operation of the device.

What is claimed is:

1. A device for measuring intraocular pressure, comprising a housing; a movable bushing having a support, said movable bushing being placed within the housing and adapted to reciprocate therein within a limited range to apply a static load to the eyeball through the eyelid; a rod with a flat base, said rod being placed within the bushing to reciprocate relative, to the support and apply an impact force to deform the eyeball through the eyelid; and at least one measuring winding provided within the movable bushing, wherein the device is provided with a permanent magnet fitted on the rod, and the measuring winding is positioned relative to the permanent magnet so as to control the direction and speed of movement of the rod, said measuring winding being connected to a control, processing, and indication unit adapted to produce a voltage of opposite polarities across the measuring winding to retract the rod by an electromagnetic field to its initial position and thereafter to apply a pulse to cause the rod to move toward the support, signal from the measuring winding being converted to measure intraocular pressure and display the results, wherein the device is provided with a contactless indicator giving an indication of a specified static load being applied to the eyeball through the eyelid during measurement.

2. A device as claimed in claim 1, wherein said indicator is a sensor showing the position of the bushing in relation to the housing.

3. A device as claimed in claim 2, wherein the sensor showing the position of the movable bushing in relation to the housing comprises a generator, an additional bushing with a cavity, and a coil mounted on the movable bushing and the housing, respectively, to vary the inductance of the coil winding during the movement of the movable bushing, the winding of the coil being connected to the generator circuit.

4. A device as claimed in claim 3, wherein the generator of the sensor showing the position of the movable bushing in relation to the housing is connected to the control, processing, and indication unit.

5. A device as claimed in claim 1, wherein the flat base of the rod has an area of 0.2 to 1.5 $mm^2$.

6. A device as claimed in claim 1, wherein the support is of a detachable type.

7. A device as claimed in claim 1, wherein the support comprises two inwardly curved wedge-shaped projections having rounded ends, with a leveling annular projection provided between said rounded ends at a height of 3 to 5 mm from their base.

8. A device as claimed in claim 1, wherein the movable bushing and support have cavities and apertures for air to be exhausted during the movement of the rod.

* * * * *